United States Patent
Lipsey

(10) Patent No.: US 11,079,367 B2
(45) Date of Patent: Aug. 3, 2021

(54) METHOD AND APPARATUS FOR ASSESSING THE CURRENT STATE OF DONENESS OF A COOKING FOOD ITEM

(71) Applicant: Samuel Elliot Lipsey, McLean, VA (US)

(72) Inventor: Samuel Elliot Lipsey, McLean, VA (US)

( * ) Notice: Subject to any disclaimer, the term of this patent is extended or adjusted under 35 U.S.C. 154(b) by 57 days.

(21) Appl. No.: 16/501,380

(22) Filed: Apr. 4, 2019

(65) Prior Publication Data
US 2019/0234925 A1    Aug. 1, 2019

Related U.S. Application Data

(62) Division of application No. 15/330,576, filed on Oct. 14, 2016, now abandoned.

(51) Int. Cl.
| | |
|---|---|
| *G01N 33/02* | (2006.01) |
| *B26D 3/18* | (2006.01) |
| *B26F 1/16* | (2006.01) |
| *B26F 1/44* | (2006.01) |

(52) U.S. Cl.
CPC ............... *G01N 33/02* (2013.01); *B26D 3/18* (2013.01); *B26F 1/16* (2013.01); *B26F 1/44* (2013.01)

(58) Field of Classification Search
CPC ................. B26D 3/18; B26F 1/16; B26F 1/44
USPC .......... 99/345, 485, 532, 544, 576, 577, 582
See application file for complete search history.

(56) References Cited

U.S. PATENT DOCUMENTS

| | | | | |
|---|---|---|---|---|
| 2005/0044971 A1* | 3/2005 | Harris | ...................... | G01N 1/04 |
| | | | | 73/864.43 |
| 2016/0166761 A1* | 6/2016 | Piehl | .................. | A61M 5/1408 |
| | | | | 604/506 |

* cited by examiner

*Primary Examiner* — Phuong T Nguyen

(57) ABSTRACT

A method and apparatus is provided for assessing the current state of doneness of a cooking food item. In a preferred embodiment, a sharpened hollow tubular cutting member of relatively small diameter is rotationally activated to cut and remove from a cooking food item a cylindrical core sample, preferably throughout its entire thickness, without substantial distortion of the shape of the sample. Upon expulsion from the cutting member, inspection of the core sample permits visual determination of the current state of doneness of the food item.

2 Claims, 2 Drawing Sheets

METHOD AND APPARATUS FOR ASSESSING THE CURRENT STATE OF DONENESS OF A COOKING FOOD ITEM

CROSS-REFERENCE TO RELATED APPLICATION

This is a divisional of U.S. application Ser. No. 15/330,576, filed on Oct. 14, 2016, the disclosure of which is incorporated herein in its entirety.

BACKGROUND AND OBJECT OF THE INVENTION

Field of the Invention

A problem that has plagued man since the discovery of fire has been the difficulty of assessing the doneness of a food item whose contents are cooked by or with the use thereof. An object of the present invention is to provide a simple and effective apparatus and method for sampling and visually observing the cross section of a cooking food item in order to assess its degree of doneness without significant aesthetic damage to the food item, without significant loss of interior juices, and without exposure of significant new surface area to the heated environment.

When it comes to the doneness of a particular food item, each individual has different preferences. Thus, terms like "rare," "medium rare," "medium well," and "well done" have crept into the vocabulary of food preparers in an effort to facilitate communication of these preferences between food preparer and food consumer. Communication of the preference, however, merely defines the problem. A food preparer must be able to determine, during the cooking process, when that degree of doneness has been attained. More specifically, the preferred degree of doneness reflects the heat history, consistency, and appearance of the center of the food item, which remains invisible to the food preparer during the cooking process.

Proper assessment of the degree of doneness of a food item can be and often is more than a matter of aesthetic preference. Many items, if undercooked, carry the danger of food-borne illness. For example, undercooked ground beef carries the risk of *E. coli* contamination due to exposure of the ground beef, even in the center of the food item, to contaminated materials in the manufacturing process. Similarly, undercooked poultry, particularly chicken, carries the risk of foodborne *Salmonella* poisoning.

Master chefs have often acquired through extensive experience the ability to determine the degree of doneness of a food item by pressing against its cooked surface. This level of experience and skill is in most instances beyond that of most food preparers. The rest of us have historically resorted to a variety of surrogates in an effort to assess the doneness of the food item. First among these is the use of cooking time. Every "backyard chef" has his or her recipe: "3 minutes per side for rare," "5 minutes per side for medium," "8 minutes per side for well done," and the like. The problem with this method is that it highly depends on the temperature of the cooking surface, the uniformity of the temperature of the cooking surface, the thickness of the food item, as well as its configuration and density. All of these parameters can be highly variable, leading at times to grossly inaccurate results.

Another surrogate widely used in an attempt to assess doneness of a food item is the "meat thermometer." Again, individual food preparers have their own benchmarks. The Weber Grill Company, for example, recommends the following:

| | |
|---|---|
| Beef - medium rare | 145° F. |
| Beef - well done | 170° F. |
| Pork - medium | 160° F. |
| Pork - well done | 170° F. |
| Ham | 140° F. |
| Poultry - well done | 180° F. |
| Lamb - medium rare | 150° F. |
| Lamb - medium | 160° F. |

The problem with this technique, however, lies less in identification of the benchmark temperature than in actually assessing it with instruments of highly variable accuracy by users with highly variable experience. Many inexpensive meat thermometers are simply inaccurate. Even expensive meat thermometers suffer from the problem that the temperature sensing probe is exposed not only to temperatures within the meat, but also to high temperatures above the cooking surface, which can distort the reading. Even more problematic is the proper identification of where and how deeply to insert the probe in-food items with variable thickness and configuration. As a result, almost every food preparer owns a meat thermometer, yet very few actually use them.

Inadequacies of the forgoing surrogates for the assessment of doneness have lead to widespread use of the only direct technique for assessing the doneness of a food item in the prior art—cutting the item open and inspecting the color and appearance of the interior directly. This technique suffers from a variety of shortcomings. First, it visually and physically damages the food item being prepared in a significant, irreversible, and unappealing way. Second, major incisions, often tantamount to cutting the item in half, lead to dramatic losses of retained juices, directly proportional to the newly exposed surface area. Moreover, this newly exposed surface provides yet additional heat exposure to the food item, whereby subsequent assessment of its doneness (with yet another incision) is no longer representative of the condition of other, undisturbed, food items being prepared concurrently.

SUMMARY OF THE INVENTION

In view of the forgoing, there is a need for a method and apparatus to reliably ascertain the degree of doneness on the interior of a cooking food item with accuracy and without undue perturbation of the food item. The present invention addresses this need by providing a method and apparatus for sampling a small diameter core specimen, preferably through the entire thickness of the food item. Upon removal from the apparatus and inspection this core specimen provides an accurate visual assessment of the interior condition of the cooking food item, without significant aesthetic damage to the food item, without significant loss of interior juices, and without exposure of significant new surface area to the heated environment.

DETAILED DESCRIPTION OF THE INVENTION

Figure 1:
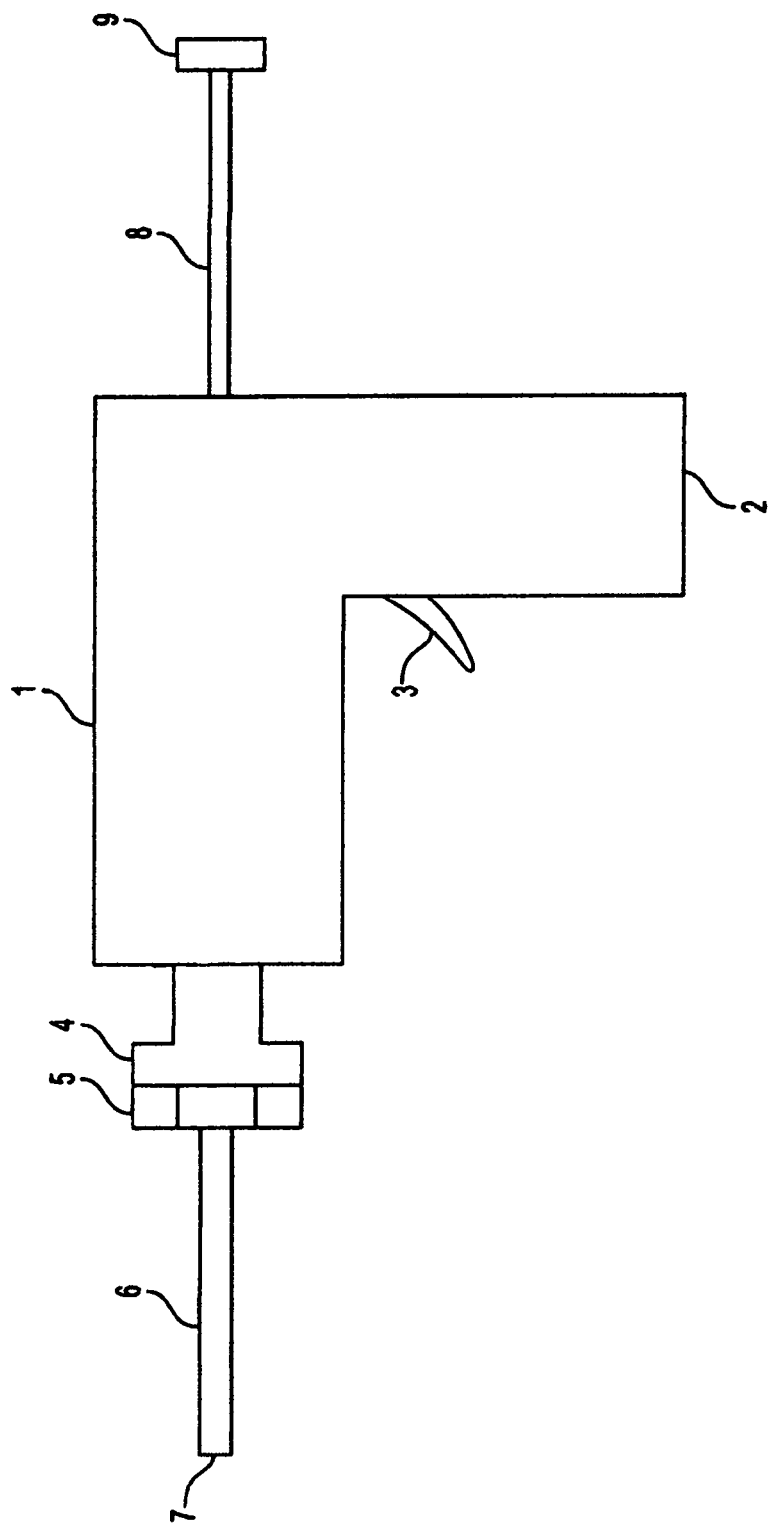
FIG. 1 is an exterior view of one embodiment of a device in accordance with the present invention.

The objects of the present invention are attained through a method and apparatus permitting extraction of a small diameter core sample of the food item while it is cooking which, upon removal from the extraction device, allows rapid and accurate visual assessment, in real time, of the current degree of doneness of the cooking food item by assessment of the color and condition of the food item, preferably throughout its thickness. In its broadest respects, the invention involves penetration through the thickness of the food item of a sharpened, small diameter, rigid tube whereby a small diameter cylindrical sample of the food item is cut from the remainder of the item and lodged fixedly within the extraction tube so that upon removal of the extraction tube from the food item, the core remains lodged in the extraction tube. Subsequent expulsion of the intact cylindrical sample from the extraction tube by mechanical or hydraulic means allows visual inspection and assessment of degree of doneness, preferably across the entire cross section of the food item. That appearance can be judged and correlated with the current degree of doneness of the food item either against the user's own experience with the particular food item, or by comparison to a chart of standard photographic samples extracted using the invention from the type of food item being prepared and labeled in accordance with the corresponding degree of doneness.

It has been found in practice that the diameter of the extraction tube and the configuration of its penetrating edge are important to the successful practice of the invention. The diameter must be large enough so that it actually cuts a sample of the food item away from the remaining body of the item rather than penetrating the item by displacing material to the side in the manner of a hypodermic needle. In this regard, it has been found that the leading edge of the extraction tube must be sharp but, as was the case with its diameter, must be sharpened in a way that results in excising material from the desired thickness of the food item. Many hypodermic needles, as well as basting needles, intended merely to penetrate the skin without removing a sample thereof, are sharpened simply by cutting hollow, tube-shaped needle diagonally at its end. While such constructs are suitable for sampling dense, firm food items, they are not preferred for use on softer food items, such as most meat, poultry, and fish. Rather, it has been determined that the leading edge of the extraction tube is preferably sharpened, preferably along its inner annular edge, whereby a knife-like cutting function is performed by the inner annular edge, thus ensuring the creation of a cylindrical core sample lodged within the extraction tube.

The inside and outside diameters of the extraction tube should ideally be as close to each other as possible, while still maintaining the structural integrity of the extraction tube. While the size of the core sample extracted will be dictated by the inside diameter of the extraction tube, and is theoretically limited only by the sharpness and structural strength of the extraction tube, it has been found that most food items are sufficiently heterogeneous in internal structure that a somewhat larger core sample is useful in visually assessing their degree of doneness. Thus, extraction tubes with inside diameters varying from about 2 to about 7 millimeters are preferred, with about 4 to about 5 millimeters being particularly preferred, for sampling most common cooked food items such as beef, pork, lamb, poultry, and fish.

The length of the extraction probe is dictated by the thickness of the food item to be sampled. Most cooked food items rarely exceed 8 centimeters (roughly 3 inches) in thickness so extraction tube lengths from about 5 to about 13 centimeters (roughly 2-5 inches) are preferred with about 7.5 centimeters (roughly 3 inches) being particularly preferred.

The extraction tube must be inserted into or through the cooking food item in a manner that results in cutting of a cylindrical sample from the body of the food item corresponding approximately to the inside diameter of the extraction tube, and the retention of that sample within the extraction tube when the extraction tube is removed from the food item. Normally, this requires the extraction tube to penetrate fully through the thickness of the food item, whereby no residual attachment of the cylindrical sample to the food item impairs its extraction. In some instances, such as cooking whole chickens or boned chicken breasts, such through penetration is not possible. In such instances, it is normally sufficient for the extraction tube to penetrate the food item until it contacts a rigid, boney surface. Under these circumstances, relative movement between the leading edge of the extraction tube and the boney surface with which it makes contact is usually sufficient to sever any residual connection between the sample and the remainder of the food item.

Depending on the strength of the extraction tube and the sharpness of its inner leading annular edge, it is possible to cut the desired cylindrical sample by rapid, forceful penetration of the food item with the extraction tube. Such rapid forceful insertion can be done manually, as if one were puncturing the item with a fork, or can be accomplished by mechanical means. Mechanical means for forcible insertion of the extraction tube include release of spring-loaded actuator means, or pneumatically actuated insertion means. In either case, means for adjusting the depth of forceful penetration effectuated by the device can be included.

Some food items, such as well-marbled meats, are so soft and pliable, particularly when not well cooked, that the use of forceful insertion of the extraction tube causes penetration of the extraction tube through the food item in the manner of a hypodermic needle, whereby no cylindrical core sample is created, or substantial compression and deformation of the core sample, whereby its visual appearance upon subsequent extraction is no longer representative of the cross section of the food item. In such cases, it is desirable to impart rotational movement to the extraction tube to cause its sharpened leading annular edge to cut the boundaries of the cylindrical core sample in the manner of a moving knife blade. In this embodiment, the extraction tube can be inserted more slowly, allowing the rotational movement thereof to cut the cylindrical sample core as the extraction tube is gradually inserted through the cooking food item. Upon removal of the extraction tube, the resulting rotationally cut core sample is not compressed, and remains representative of the cross section of the cooking food item.

In cases requiring rotational cutting of the cylindrical core sample, it has been found that rotational torque is more important and in fact more desirable than high rotational speed. While rotational motion of the extraction tube can be imparted by any suitable means, including mechanical means in the nature of a hand drill or wound spring mechanism, it is preferably imparted by a small, high speed, battery operated electric motor with appropriate gearing to adjust the speed and torque of rotational movement. The very property of food items requiring this approach, heterogeneity of structure and malleability in undercooked states, requires that rotational cutting energy be applied forcefully, but only at moderate speed. The torque and operating speed roughly equivalent to that of a hand-held, light-duty, battery-operated screwdriver powered by two AAA batteries has been found to be sufficient. Preferably, the rotational speed is from about 50 to about 200 rpm, more preferably from about 100-200 rpm, and most preferably from about 140 to about 175 rpm. In practice, the applied rotational torque preferably can vary from about 0.06 to about 0.15 lb.-ft.

In the embodiment relying upon rotational movement of the extraction tube, it is preferred that the leading edge of the extraction tube be substantially perpendicular to the longitudinal axis of the tube, and be uniformly sharpened around its inside annular edge. This configuration allows facile cutting of cylindrical core samples not only through the entire thickness of the food item when cooked on a perforated surface such as a grill, but also through the entire thickness of the food item when cooked on a solid surface, such a cast-iron pan. The rotational movement of the cutting surface acts to sever the cylindrical sample from even solid surfaces upon which it is resting, or bony surfaces juxtaposed to the sampled section in items such as boned chicken breasts. For use on non-stick cookware, it is preferred that the leading edge of the extraction tube be provided with a finely serrated hard plastic leading edge, which can cut through the food item to be sampled without damaging cooking surfaces with which it may come in contact.

Upon removal of the extraction tube, from the cooking food item with the cylindrical core sample lodged fixedly therein, visual inspection of the core sample requires its removal from the extraction tube. This may be accomplished by a variety of hydraulic, pneumatic, or mechanical means. Each of these expulsion means operates through an opening at the trailing end of the extraction tube, with a diameter substantially equal to and being axially aligned with the inside surface of the extraction tube. The expulsion opening may be associated with a reservoir cylinder filled with air, water, or a food-grade oil, such as olive oil, canola oil, vegetable oil, and the like, in operative engagement with manual or electrically activated piston means for generating pressures sufficient to expel the cylindrical core sample onto a suitable observation platform, such as a plate.

Hydraulic and pneumatic expulsion means suffer from the difficulty of controlling the speed at which the cylindrical core sample is expelled and difficulties attending expulsion of any hydraulic fluid used to do so. Accordingly, it is preferred that the expulsion means be a rigid piston with an outside diameter corresponding substantially to the inside diameter of the extraction tube coupled via an extending actuating plunger axially aligned with the piston and the extraction tube. In this embodiment, gentle pressure applied to the distal end of the actuating plunger can gently expel the cylindrical core sample onto the viewing platform while substantially preserving its shape as representative of the cross section of the cooking food item.

In practice, it has been found that operation of the apparatus and practice of the method of the present invention is substantially facilitated by the use of appropriate lubrication means, on both the inside surface and the outside surface of the extraction tube. Lubrication of the inside surface of the extraction tube is important in avoiding compression and distortion of the cylindrical sample, particularly in the forceful insertion embodiments. Lubrication of the outside surface of the extraction tube is useful in the forceful insertion embodiments to avoid simple displacement of the food item in the manner of a hypodermic needle. Lubrication of both surfaces of the extraction tube is particularly useful in the rotating insertion embodiments to allow the rotational cutting movement of the extraction tube without damaging the appearance of the cylindrical core sample. Lubrication of the outside surface of the extraction tube is particularly important in sampling fatty food items such as marbled meats. In the cooking process, the fat in the meat tends to melt and coat the outside surface of the extraction tube as it enters the food item. Upon removal of the extraction tube from the food item, and the reduction of its temperature by exposure to the ambient environment, these melted fats tend to solidify on the outside surface of the extraction tube, creating a tacky surface that can impede subsequent sampling operations.

Because the apparatus and method of the present invention are used in conjunction with food, any lubricating materials used in practicing the invention must be safe for human consumption. Accordingly, lubricating materials for use on the inside and outside surfaces of the extraction tube include food grade oils, such as olive oil, canola oil, vegetable oil, and the like. It is particularly preferred that anti-stick agents such as soybean lecithin be included in these lubricating materials. Preferably, means to replenish the lubricating medium on the interior and exterior surface of the extraction tube can be provided, either as a component of the device or as an exterior accessory, such as a storage and holding container for the extraction tube device filled with an appropriate lubricating material. When applied through means which are part of the apparatus, suitable, refillable reservoir means to hold a quantity of the lubricating fluid are provided with intermittently activatable distribution means to apply the lubricating fluid to the inside and outside surfaces of the extraction tube.

Figure 2:
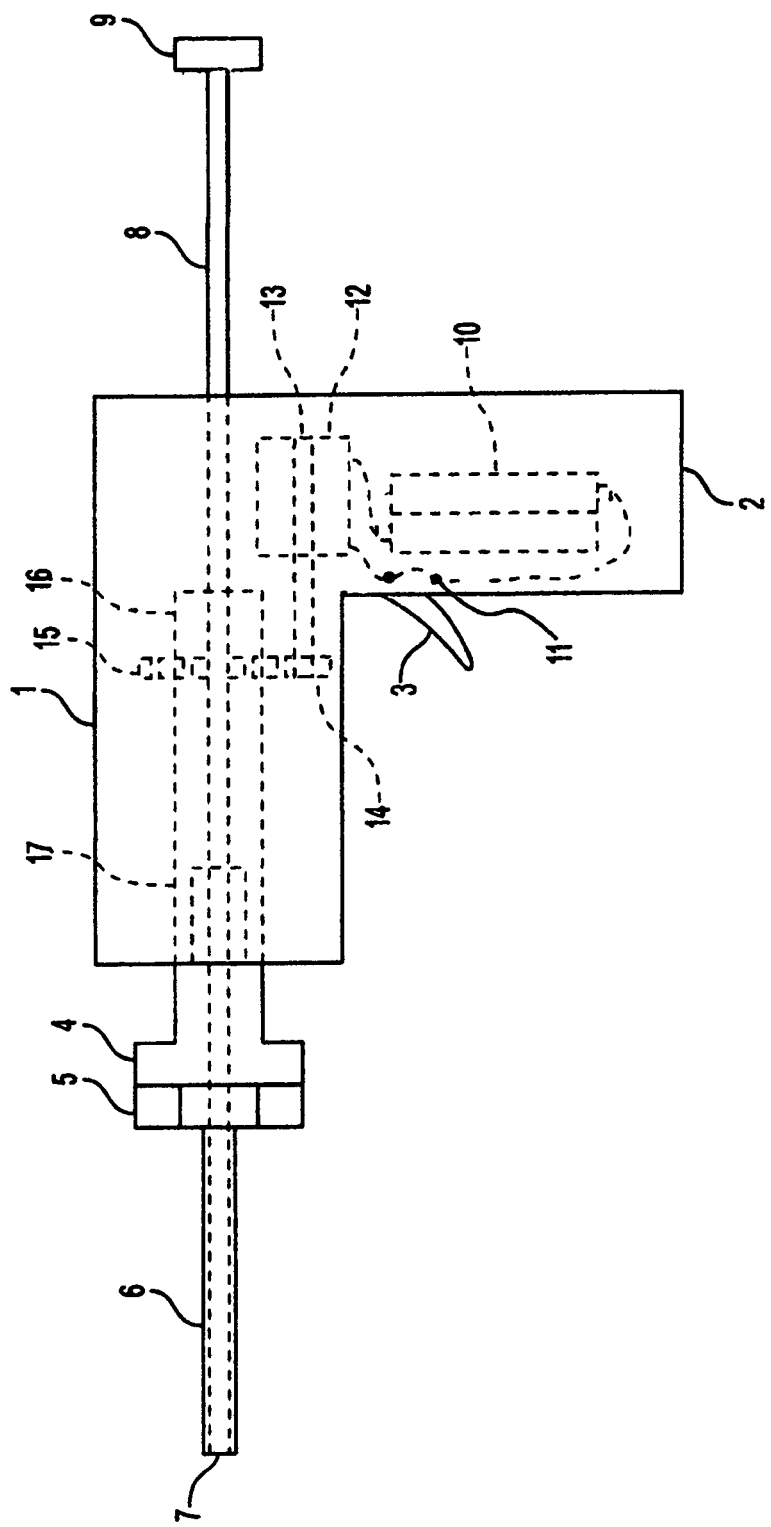
FIG. 2 illustrates representative internal mechanisms for a device achieving the objects of the present invention.

A preferred embodiment according to the present invention is illustrated in FIGS. 1 and 2. FIG. 1 is an exterior view of a device embodying the present invention. FIG. 2 shows the internal structure of the device.

As shown, the device has a unitary body 1 generally L-shaped in configuration with a horizontally extending housing portion and a vertically extending handle portion. The handle portion of body 1 contains at its base a closeable opening 2 for the insertion and removal of batteries 10 to power the device, as well as an external trigger switch 3 for activating the device. The body 1 contains an electrical power supply, preferably in the form of batteries 10, a compact, high-speed electric motor 12, and an axially mounted, hollow drive shaft 16 engaged with the motor shaft 13 by gearing 14, 15 appropriate to induce rotation of the drive shaft 16 at a speed and with torque approximating that of a light-duty electric screwdriver. The hollow drive shaft 16 ends substantially flush with the horizontally extending body portion and provides a hexagonally shaped recess 17 larger than but concentric with the hollow center of drive shaft 16 and adapted to removably receive the hollow hexagonally-shaped end of an intermediate drive member 4. The opposite end of intermediate drive member 4 is externally threaded to removably receive an internally threaded end of the hollow tubular sampling member 7. The working end of sampling member 16 is preferably sharpened, preferably on its interior leading edge.

In operation, actuation of switch 3 causes the shaft 13 of motor 12 to spin at high speed, in turn causing hollow drive shaft 16 to rotate at lower speed but with higher torque through gears 14 and 15. Rotating drive shaft 16 causes rotation of intermediate drive member 4 and sharpened sampling member 6, whereby application of gentle pressure of the sharpened edge of sampling member 6 to the surface of a cooking food item will result in cutting and retaining within the hollow tubular body of sampling member 6 a cylindrical core sample of the cooking food item, preferably throughout its thickness. The sampling member 6 is then withdrawn from the cooking food item, preferably while continuing powered rotation thereof. The resulting cylindrical core sample is then expelled from the sampling member 6 for visual assessment of the then current doneness of the food item by actuation of sample expulsion means 8 by manually applying gentle pressure to plunger end 9. The expulsion means 8 is tubular in shape but solid so as to provide uniform pressure to the surface of the cylindrical core sample. The expulsion means 8 has an outside diameter slightly smaller than the inside diameter of sampling member 6 and has a length and is mounted to permit a range of motion sufficient to fully expel the cylindrical core sample.

Sampling member 6 can be separated for cleaning from intermediate drive member 4 by means of the threaded connection between them. Intermediate drive member 5 can be separated from hollow drive shaft 16, either for cleaning or for attachment thereto of alternatively sized or configured sampling members 6, by slidably removing its externally hexagonally shaped end from the internally hexagonally shaped end of hollow drive shaft 16. The expulsion member 8 can be removed for cleaning by withdrawing its full length rearwardly from the device body 1.

It is to be understood that the foregoing Figures and descriptions are illustrative only and that the full scope of the invention is reflected in the appended claims.

What is claimed is:

1. A method for assessing the current state of doneness of a cooking food item comprising:
    selecting a food item to be cooked selected from the group consisting of meat, poultry, and fish;
    exposing said food item to heat from a cooking surface sufficient to initiate the cooking thereof;
    periodically sampling during the cooking process a cylindrical transverse cross-section of the cooking food item while heat continues to be applied to the food item from the cooking surface by contacting the exposed outer surface of the cooking food item with an electrically-driven, rotating cylindrical extraction tube, with a length sufficient to pass through the entire transverse thickness of the cooking food item, an interior diameter of from about 4 mm to about 5 mm, a sharpened interior edge on the entire circumference of the end of the tube contacting the outer surface of the cooking food item, and a coating of a food-grade oil on the exterior and interior surfaces of the extraction tube;
    applying sufficient pressure to the rotating sampling tube to effect cutting through the entire transverse thickness of the cooking food item without distorting the shape of the severed cylindrical sample formed inside the extraction tube;
    withdrawing the extraction tube and the transverse cross-sectional sample contained within it from the cooking food item while continuing the powered rotation thereof and while continuing to heat the cooking food item;
    expelling said transverse cross-sectional sample from the extraction tube by activation of a piston slideably mounted inside the extraction tube by application of force to the opposite end of the piston sufficient to expel the entire sample onto a viewing platform while preserving the sample's cylindrical shape as representative of the cross-section of the cooking food item;
    inspecting the gradations of color across the longitudinal length of the expelled cylindrical sample corresponding to the transverse thickness of the cooking food item to assess the current state of doneness of the cooking food item; and
    removing the cooking food item from the heated cooking surface when the visual inspection of the most recently expelled cylindrical sample reflects the desired state of doneness of the cooking food item.

2. A method according to claim 1 wherein the assessment of the state of doneness is conducted by comparison of the expelled cylindrical sample to a chart of standard images of cross-sectional cores extracted using the method of claim 1 from the type of food item being cooked, labeled in accordance with the corresponding degree of doneness.

* * * * *